United States Patent [19]

Kamogawa et al.

[11] Patent Number: 4,814,305

[45] Date of Patent: Mar. 21, 1989

[54] METHOD FOR REGENERATION OF OXIDATION CATALYST

[75] Inventors: Masatake Kamogawa; Masaaki Kato, both of Otake, Japan

[73] Assignee: Mitsubishi Rayon Co., Ltd., Tokyo, Japan

[21] Appl. No.: 119,506

[22] Filed: Nov. 12, 1987

[30] Foreign Application Priority Data

Nov. 20, 1986 [JP] Japan ................. 61-277530

[51] Int. Cl.[4] .............. B01J 27/28; B01J 38/66; C07C 57/055; C07C 51/235
[52] U.S. Cl. .................... 502/26; 502/29; 502/211; 562/535
[58] Field of Search .............. 502/26, 27, 29, 211

[56] References Cited

U.S. PATENT DOCUMENTS

| | | | |
|---|---|---|---|
| 4,165,296 | 8/1979 | Ishii et al. | |
| 4,303,550 | 12/1981 | Callahan et al. | 252/413 |
| 4,321,160 | 3/1982 | Farrington et al. | |
| 4,410,450 | 10/1983 | Sasaki et al. | 502/27 |
| 4,471,062 | 9/1984 | Farrington et al. | |
| 4,604,370 | 8/1986 | Sarumaru et al. | |
| 4,707,460 | 11/1987 | Ishii et al. | 502/26 |

FOREIGN PATENT DOCUMENTS 2029719A  3/1980  United Kingdom .

Primary Examiner—Paul E. Konopka
Attorney, Agent, or Firm—Armstrong, Nikaido, Marmelstein & Kubovcik

[57] ABSTRACT

A method for regenerating a phosphorus-, molybdenum- and alkali metal-containing oxidation catalyst spent in the production of an unsaturated carboxylic acid by vapor-phase oxidation of an unsaturated aldehyde, which comprises treating the deactivated catalyst with aqueous ammonia and an aqueous solution containing at least one of a nitrogen-containing heterocyclic compound, an amine, and ammonium carbonate, followed by drying and calcining the treated catalyst.

11 Claims, No Drawings

METHOD FOR REGENERATION OF OXIDATION CATALYST

FIELD OF THE INVENTION

The present invention relates to a method for regenerating a phosphorus-, molybdenum- and alkali metal-containing catalyst which has been spent in the production of an unsaturated carboxylic acid by vapor-phase oxidation of an unsaturated aldehyde.

DESCRIPTION OF THE RELATED ART

Catalysts are often deactivated during use, for example, the deactivation is caused suddenly by an abnormal reaction in the course of normal reaction or gradually as the catalyst structure changes during long-term continuous operation. Sometimes catalysts deteriorate when subjected before use to heat treatment at excessively high temperatures.

Also about catalysts for the production of unsaturated carboxylic acids by the vapor-phase oxidation of unsaturated aldehydes, a number of methods are proposed for the regeneration of catalysts which have been deactivated by various causes. For example, there are proposed the methods of treating with ammonia and water (Japanese patent application Laid-Open No. 33082/72) and the method of treating with hydrochloric acid (Japanese patent application Laid-Open No. 2293/79). These methods, however, are not much satisfactory in regeneration efficiency, treating, operation, and economy, further improvements thereof being desired.

On the other hand, some of the present inventors have proposed a regeneration method in Japanese patent application Laid-Open No. 11379/78 (corresponding to U.S. Pat. No. 4,165,296) which comprises treating a phosphorus-, molybdenum- and alkali-containing catalyst with aqueous ammonia and aqueous hydrogen peroxide. However, the catalyst regenerated by this method is insufficient in service life though excellent in the result of the initial stage catalystic reaction. Hence, further improvements of this method are desired.

SUMMARY OF THE INVENTION

With regard to such a phosphorus-, molybdenum- and alkali metal-containing catalyst for the production of an unsaturated carboxylic acid by vapor-phase oxidation of an unsaturated aldehyde, the present inventors made intensive studies with the object of providing an industrially advantageous regeneration method by which the catalyst when deactivated by various causes, could recover its activity and further retain the activity steadily for a long period of time. As a result it has been found that a highly active catalyst can be regenerated by treating the deactivated catalyst with aqueous ammonia and an aqueous solution containing at least one of a nitrogen-containing heterocyclic compound, an amine, and ammonium carbonate, in the presence, if necessary, of nitrate ions and/or either aqueous hydrogen peroxide or ozone. Based on this finding, the present invention has been accomplished.

DESCRIPTION OF THE PREFERRED EMBODIMENT

A preferred embodiment of the present invention is as follows:

Water is added to the deactivated catalyst and aqueous ammonia is further added with stirring. This mixture is aged under stirring for a period of 30 minutes to several hours at a temperature of 40° to 80° C., and then evaporated to dryness or spray-dried. The resulting dry cake is ground and dispersed in water, and a nitrogen-containing heterocyclic compound, an amine, or ammonium carbonate is added. It is possible, of course, to use jointly two or more of these compounds. Then the mixture is aged under stirring for a period of 30 minutes to several hours at a temperatuer of 40° to 90° C., and dried. This drying is carried out by either evaporation or spraying, preferably at a temperature of at least 100° C. This dried cake is pulverized, molded by compression, and calcined at a temperature of 300° to 450° C.

The X-ray powder diffraction pattern of the thus regenerated catalyst shows spectral lines due to a phosphorus-molybdenum-alkali metal complex and practically no spectral lines due to such an oxide as molybdenum trioxide that are given by the deactivated catalyst. That is to say, the regenerated catalyst gives an X-ray diffraction spectrum equal to that of the original highly active catalyst.

The deactivated catalyst to which the method of the present invention is applied contains phosphorus, molybdenum and alkali(s) and may further contain one or more other elements. Desirable atomic ratios of phosphorus and other elements to molbdenum in the original or regenerated catalyst when the molybdenum content is taken as 12 are 0.01 to 3 of phosphorus, 0.2 to 5 of the whole alkali metal and 0 to 10 of the whole other element.

Preferred alkali metals in particular, are potassium, rubidium and cesium. Said other elements include vanadium, silver, magnesium, zinc, selenium, tellurium, arsenic, copper, germanium, iron, nickel, silicon, rhodium, tungsten, boron, bismuth, aluminum, tantalum, chromium, barium, antimony, tin, and thallium.

While catalysts having the above compositions when used in the production of unsaturated carboxylic acids from unsaturated aldehydes may be deactivated by such causes as stated before, the method of the present invention can be applied to the catalysts deactivated by all the causes that happen in the industrial produciton.

Suitable amounts of aqueous ammonia for the regeneration treatment depend upon the state of the deactivated catalyst. Generally the amount of ammonia is up to 100 moles, preferably from 6 to 60 moles, per 12 gram atoms of molybdenum contained in the deactivated catalyst. Out of this range, the function of the regenerated catalyst is inferior. Though the reason for this is not clear, this is caused conceivably by an undesirable complex compound formed when excessive ammonia is used.

At least one of a nitrogen-containing heterocyclic compound, an amine, and ammonium carbonate can be added preferably after the dry powder treated with aqueous ammina as stated above has been dispersed in water, though the addition at the treatment with aqueous ammonia is possible.

Nitrogen-containing heterocyclic compounds or amines which can be used include, for example, pyridine, piperazine, pyrimidine, pyrazine, piperazine, triethylamine, triethanolamine, and hydrochlorides, sulfates and nitrates of them.

Any of these compounds is used in an amount of 0.5 to 60 moles, preferably 1 to 36 moles, per 12 gram atoms of molybdenum contained in the deactivated catalyst.

Departing from this range results in a regenerated catalyst having insufficient functions.

In the present invention, the regenerating treatment, when carried out in the presence of nitrate ions and/or either hydrogen peroxide or ozone, may produce favorable effects. In particular, the catalyst, when deactivated by reducing action, can be regenerated effectively by treatment in the presence of hydrogen peroxide or ozone. Preferably, up to 5 moles of nitrate ions or up to 7 moles of hydrogen peroxide or ozone is used per 12 gram atoms of molybdenum. Exceeding the above limit decreases the effect.

There is no particular restriction on the unsaturated aldehyde to which the catalyst regenerated by the method of the present invention is applied, but preferred unsaturated aldehydes are acrolein and methacrolein.

In the vapor-phase oxidation, the proportions of the unsaturated aldehyde and oxygen can be widely varied, while it is desirable that each of their proportions be in the range of 1 to 20 mole% and the proportion of inert gas be in the range of 60 to 98%.

Normally, reactants are charged with themselves diluted with an inert gas such as nitrogen, steam or carbon dioxide. In particular, the presence of steam may increase the yield of the objective unsaturated acid.

The reaction may be carried out under atmospheric pressure or somewhat reduced or elevated pressure, e.g. 0.5 to 20 atm. (absolute pressure).

The reaction temperature is in the range of 200° to 450° C., preferably 240° to 400° C.

The present invention is illustrated in more detail with reference to the following examples and comparative examples. In these examples, parts are all by weight.

Therein, catalysts were evaluated normally under the following conditions: A prescribed amount of catalyst was filled in a reactor, and a gas mixture of 5% of an unsaturated aldehyde, 10% of oxygen, 30% of steam, and 55% of nitrogen (all mole %) was passed through the reactor at a prescribed temperature and a space velocity of 2000 l/hr. The conversion, selectivity, and single-pass yield are defined as follows:

$$\text{Conversion} = \frac{\text{Moles of reacted aldehyde}}{\text{Moles of fed aldehyde}} \times 100$$

$$\text{Selectivity} = \frac{\text{Moles of produced unsaturated carboxylic acid}}{\text{Moles of reacted aldehyde}} \times 100$$

$$\text{Single-pass yield} = \frac{\text{Moles of produced unsaturated carboxylic acid}}{\text{Moles of fed aldehyde}} \times 100$$

EXAMPLE 1

(Preparation of catalyst)

424 parts of ammonium paramolybdate was dissolved in 2000 parts of 60° C. water, and 46.1 parts of 85% phosphoric acid, diluted with 100 parts of water, was added to the solution with stirring. Thereto were further added a solution of 14.8 parts of rubidium nitrate in 100 parts of water and then a solution of 100 parts of chromium trioxide in 50 parts of water. After 5 minutes' retention of the mixture, 3.4 parts of silver nitrate dissolved in 20 parts of water was added. The resulting mixture was evaporated with stirring to dryness. The obtained solid matter was dried at 120° C. for 16 hours, finely pulverized, molded by compression, and calcined at 400° C. for 5 hours in a stream of air, giving a highly active catalyst. The atomic ratios of metallic elements in this catalyst are represented by $P_2Mo_{12}Rb_{0.5}Cr_{0.5}Ag_{0.1}$.

Using this catalyst, methacrolein was subjected to continuous oxidation, wherein the reaction temperature was raised intentionally to cause an abnormal reaction, thereby deactivating the catalyst. Thus a deactivated catalyst was obtained.

(Regeneration of deactivated catalyst)

100 Parts of the deactivated catalyst with 200 parts of water was stirred for 10 minutes, and thereto was added dropwise 37 parts of 28% aqueous ammonia. The mixture was maintained at 50° C. for 1 hour under stirring, and evaporated to dryness. The resulting solid matter was dried at 120° C. for 16 hours, pulverized, and added to 200 parts of water. The mixture was stirred for 30 minutes, and 95 parts of pyridine was dropped gradually thereinto. Further the mixture was stirred at 90° C. for 30 minutes, and as stated above, it was evaporated to dryness and then further dried. Thereafter, the dry solid was molded and calcined, as in the preparation of the highly active catalyst, giving a regenerated catalyst.

Methacrolein was oxidized in the presence of each of these three catalysts. Results of the reaction are shown in Table 1.

TABLE 1

| Type of catalyst | Reaction period (hr) | Reaction temperature (°C.) | Conversion of methacrolein (%) | Selectivity for methacrylic acid (%) | Single-pass yield of methacrylic acid (%) |
|---|---|---|---|---|---|
| Highly active catalyst | 5 | 275 | 68.0 | 79.0 | 53.7 |
| Deactivated catalyst | 15 | 275 | 7.5 | 74.1 | 5.6 |
|  | 17 | 304 | 41.1 | 70.0 | 28.8 |
| Regenerated catalyst | 5 | 275 | 67.5 | 80.0 | 54.0 |
|  | 1600 | 275 | 65.1 | 79.1 | 51.5 |

EXAMPLES 2 AND 3

The same deactivated catalyst as prepared in Example 1 was regenerated according to the procedure of Example 1 but using 179 parts of triethanolamine and 23 parts of ammonium carbonate each in place of pyridine. Results of the reaction conducted to evaluate these regenerated catalysts were as shown in Table 2.

TABLE 2

| Example No. | Reagent added besides aqueous ammonia | Reaction temperature (°C.) | Conversion of methacrolein (%) | Selectivity for methacrylic acid (%) | Single-pass yield of methacrylic acid (%) |
|---|---|---|---|---|---|
| 2 | triethanolamine | 275 | 67.2 | 78.8 | 53.0 |
| 3 | Ammonium carbonate | 275 | 66.9 | 78.0 | 52.2 |

EXAMPLE 4

200 Parts of water was added to 100 parts of the same deactivated catalyst as used in Example 1, and stirred for 10 minutes. Thereto was added dropwise 37 parts of 28% aqueous ammonia. The mixture was maintained at 50° C. for 1 hour under stirring, and 95 parts of pyridine was dropped gradually thereinto. The resulting mixture was maintained at 90° C. for 30 minutes under stirring, evaporated to dryness, and further dried at 120° C. for 16 hours. The dry cake was pulverized, molded by compression, and calcined at 400° C. for 5 hours in a stream of air. Thus a regenerated catalyst was obtained.

Methacrolein was oxidized in the presence of this catalyst. Results of the reaction are shown in Table 3.

EXAMPLE 5

A regenerated catalyst was prepared according to the procedure of Example 4 but using 47 parts of pyridine and 60 parts of triethylamine in place of 47 parts of pyridine. Results of the reaction conducted in the presence of this regenerated catalyst are shown in Table 3.

COMPARATIVE EXAMPLE 1

A regenerated catalyst was prepared according to the procedure of Example 4 but without adding pyridine. Results of the reaction conducted to evaluate this regenerated catalyst are shown in Table 3.

TABLE 3

| Example No. | Reagent added besides aqueous ammonia | Reaction temperature (°C.) | Conversion of methacrolein (%) | Selectivity for methacrylic acid (%) | Single-pass yield of methacrylic acid (%) |
|---|---|---|---|---|---|
| 4 | Pyridine | 275 | 66.5 | 78.5 | 52.2 |
| 5 | Pyridine and triethylamine | 275 | 67.0 | 79.0 | 52.9 |
| Comparative 1 | None | 275 | 45.5 | 71.1 | 32.3 |

EXAMPLES 6–8

(Preparation of catalyst)

424 Parts of ammonium paramolybdate and then 7.0 parts of ammonium metavanadate were dissolved in 2000 parts of 60° C. water with stirring. Thereto were added successively 23.1 parts of 85% phosphoric acid diluted with 50 parts of water, an aqueous solution of 39 parts of cesium nitrate and 4.8 parts of copper nitrate, and 10.5 parts of germanium oxide diluted with 50 parts of water. The mixture was maintained at 60° C. for 30 minutes under stirring, then evaporated to dryness, and further dried at 120° C. for 16 hours. The dry cake was finely pulverized, molded by compression, and calcined at 390° C. for 5 hours in a stream of air, giving a highly active catalyst. The atomic ratios of metallic elements in this catalyst are represented by $P_1Mo_{12}Cs_1Ge_{0.5}Cu_{0.1}V_{0.3}$.

Using this catalyst, methacrolein was subjected to continuous oxidation, wherein the reaction temperature was raised intentionally to cause an abnormal reaction, thereby deactivating the catalyst. Thus a deactivated catalyst was obtained.

(Regeneration of deactivated catalyst)

100 Parts of the deactivated catalyst and 5.2 parts of ammonium nitrate were added to 200 parts of water, and 128 parts of 28% aqueous ammonia was added dropwise to the mixture under stirring. Thereafter, the procedure of Example 1 was followed except that 95 parts of pyridine was replaced by each of 51 part of piperidine, 89 parts of triethanolamine, and 58 parts of ammonium carbonate, thus preparing regenerated catalysts. Results of the reaction conducted to evaluate these regenerated catalysts are shown in Table 4.

EXAMPLE 9

100 Parts of the same deactivated catalyst as prepared in Example 6 and 5.2 parts of ammonium nitrate were added to 200 parts of water, and 128 parts of 28% aqueous ammonia was added dropwise to the mixture under stirring. Thereafter, the procedure of Example 4 was followed except that 95 parts of pyridine was replaced by 47.5 parts of pyridine, thus preparing a regenerated catalyst. Results of the reaction conducted to evaluate this regenerated catalyst are shown in Table 4.

COMPARATIVE EXAMPLES 2 AND 3

Regenerated catalysts were prepared according to the procedure of Example 9 except that neither ammonium nitrate nor pyridine was used (in Comparative Example 2) and pyridine was not used (in Comparative Example 3). Results of the reaction conducted to evaluate these regenerated catalysts are shown in Table 4.

TABLE 4

| Example No. | Type of catalyst | Reagent added besides aqueous ammonia in regeneration | Reaction period (hr) | Reaction temperature (°C.) | Conversion of methacrolein (%) | Selectivity for methacrylic acid (%) | Single-pass yield of methacrylic acid (%) |
|---|---|---|---|---|---|---|---|
| 6 | Highly active catalyst | — | 5 | 285 | 60.0 | 88.3 | 53.0 |
| | Deactivated catalyst | — | 15 | 285 | 8.3 | 76.5 | 6.3 |
| | | | 17 | 340 | 37.9 | 79.9 | 30.3 |
| | Regenerated catalyst | Ammonium nitrate | 5 | 285 | 61.1 | 89.0 | 54.4 |
| 7 | Regenerated catalyst | Piperidine | 1600 | 287 | 60.5 | 88.1 | 53.3 |
| | | Ammonium nitrate and triethanolamine | 5 | 285 | 59.2 | 88.0 | 52.1 |
| 8 | Regenerated catalyst | Ammonium nitrate and ammonium carbonate | 5 | 285 | 58.7 | 87.9 | 51.6 |
| 9 | Regenerated catalyst | Ammonium nitrate and pyridine | 5 | 285 | 59.0 | 88.4 | 52.2 |
| Comparative 2 | Regenerated catalyst | — | 5 | 285 | 40.2 | 75.5 | 30.4 |

TABLE 4-continued

| Example No. | Type of catalyst | Reagent added besides aqueous ammonia in regeneration | Reaction period (hr) | Reaction temperature (°C.) | Conversion of methacrolein (%) | Selectivity for methacrylic acid (%) | Single-pass yield of methacrylic acid (%) |
|---|---|---|---|---|---|---|---|
| Comparative 3 | Regenerated catalyst | Ammonium nitrate | 5 | 285 | 48.9 | 82.1 | 40.1 |

EXAMPLE 10

(Preparation of catalyst)

346 parts of molybdenum trioxide was added to 2000 parts of water with stirring, and 9.1 parts of vanadium (V) oxide was added to the mixture with stirring. Thereto were added successively 23.1 parts of 85% phosphoric acid diluted with 50 parts of water, an aqueous solution containing 10.1 parts of potassium nitrate, and dropwise 134 parts of 28% aqueous ammonia. After 10 minutes' aging of the mixture, 18.9 parts of 60% aqueous arsenic acid and then an aqueous solution of 4.0 parts of chromium trioxide were added. This mixture was maintained at 80° C. for 30 minutes, evaporated to dryness and further dried at 120° C. for 16 hours. The dry cake was finely pulverized, molded by compression, and calcined at 400° C. for 5 hours in a stream of air, giving a highly active catalyst. The atomic ratios of metallic elements in this catalyst is represented by $P_1Mo_{12}K_{0.5}Cr_{0.2}As_{0.4}V_{0.5}$.

Using this catalyst, methacrolein was subjected to continuous vapor-phase oxidation for 700 hours, wherein the reaction temperature and the methacrolein concentration were raised simultaneously, on purpose, to cause an abnormal reaction, thereby deactivating the catalyst. Thus a deactivated catalyst was obtained.

(Regenerated of deactivated catalyst)

50 Parts of this deactivated catalyst and 26 parts of ammonium nitrate were added to 100 parts of water, and 75 parts of 28% aqueous ammonia was added dropwise to the mixture with stirring. Then after gradual dropwise addition of 5.1 parts of 30% aqueous hydrogen peroxide, the mixture was maintained at 80° C. for 30 minutes, evaporated to dryness, and further dried at 120° C. for 16 hours.

Thereafter, the procedure of Example 1 was followed but 95 parts of pyridine was replaced by 28 parts of pyridine, thereby preparing a regenerated catalyst. Results of the reaction conducted to evaluate these three catalysts are shown in Table 5.

EXAMPLE 11

A regenerated catalyst was prepared according to the procedure of Example 10 but using neither ammonium nor aqueous hydrogen peroxide. Results of the reaction conducted to evaluate this catalyst are shown in Table 5.

EXAMPLES 12 AND 13

Regenerated catalysts were prepared according to the procedure of Example 10 but using 32.5 parts of piperazine and 4.8 parts of ammonium carbonate each in place of 28 parts of pyridine. Results of the reaction conducted to evaluate these catalysts are shown in Table 5.

EXAMPLE 14

The procedure of Example 10 was followed except that the highly active catalyst was deactivated not by the abnormal reaction but by the heat treatment at 550° C. for 10 hours. Results of the reaction conducted to evaluate this deactivated catalyst and the regenerated catalyst are shown in Table 5.

COMPARATIVE EXAMPLE 4

A regenerated catalyst was prepared according to the procedure of Example 10 but without the treatment with pyridine. Results of the reaction conducted to evaluate this catalyst are shown in Table 5.

TABLE 5

| Example No. | Type of catalyst | Reaction period (hr) | Reaction temperature (°C.) | Conversion of methacrolein (%) | Selectivity for methacrylic acid (%) | Single-pass yield of methacrylic acid (%) |
|---|---|---|---|---|---|---|
| 10 | Highly active catalyst | 5 | 280 | 69.0 | 83.3 | 57.5 |
|  | Deactivated catalyst | 750 | 340 | 40.3 | 71.5 | 28.8 |
|  | Regenerated catalyst | 5 | 280 | 68.5 | 83.8 | 57.4 |
|  | Regenerated catalyst | 1600 | 282 | 68.9 | 83.8 | 57.7 |
| 11 | Regenerated catalyst | 5 | 280 | 67.2 | 82.9 | 55.7 |
| 12 | Regenerated catalyst | 5 | 280 | 68.2 | 83.3 | 56.8 |
| 13 | Regenerated catalyst | 5 | 280 | 68.0 | 83.2 | 56.6 |
| 14 | Deactivated catalyst | 5 | 280 | 10.8 | 71.6 | 7.7 |
|  | Regenerated catalyst | 5 | 280 | 69.5 | 82.9 | 57.6 |
| Comparative 4 | Regenerated catalyst | 5 | 280 | 68.8 | 83.7 | 57.6 |
|  | Regenerated | 1600 | 282 | 59.9 | 84.0 | 50.3 |

TABLE 5-continued

| Example No. | Type of catalyst | Reaction period (hr) | Reaction temperature (°C.) | Conversion of methacrolein (%) | Selectivity for methacrylic acid (%) | Single-pass yield of methacrylic acid (%) |
|---|---|---|---|---|---|---|
| | catalyst | | | | | |

EXAMPLES 15–18

Catalysts of metallic elemental compositions shown in Table 6 were prepared in the same manner as in Example 1. These catalysts were deactivated by raising the reaction temperature intentionally in the course of the continuous reaction. Deactivated catalysts thus obtained were treated according to the procedure of Example 10 to prepare regenerated catalysts. Results of the reaction conducted to evaluate these catalysts are shown in Table 6.

TABLE 6

| Example No. | Metallic elemental composition | Type of catalyst | Reaction temperature (°C.) | Conversion of methacrolein (%) | Selectivity for methacrylic acid (%) | Single-pass yield of methacrylic acid (%) |
|---|---|---|---|---|---|---|
| 15 | $P_{1.5}Mo_{12}K_{0.5}$ | Highly active catalyst | 285 | 58.1 | 87.1 | 50.6 |
| | $Cs_{0.5}Sb_{0.2}$ | Deactivated catalyst | 285 | 15.1 | 80.0 | 12.1 |
| | $Te_{0.2}W_{0.1}$ | Regenerated catalyst | 285 | 57.7 | 88.0 | 50.8 |
| 16 | $P_{1.3}Mo_{12}K_1$ | Highly active catalyst | 290 | 57.5 | 84.9 | 48.8 |
| | $Cu_{0.1}Mg_{0.2}$ | Deactivated catalyst | 340 | 30.4 | 81.0 | 24.6 |
| | $Al_{0.1}Ge_{0.5}$ | Regenerated catalyst | 290 | 60.0 | 84.0 | 50.4 |
| 17 | $P_2Mo_{12}Cs_1$ | Highly active catalyst | 290 | 65.2 | 82.1 | 53.5 |
| | $V_{0.7}Fe_{0.2}$ | Deactivated catalyst | 340 | 33.3 | 75.0 | 25.0 |
| | $Zn_{0.5}Rh_{0.01}$ | Regenerated catalyst | 290 | 64.0 | 83.0 | 53.1 |
| 18 | $P_1Mo_{12}Cs_{0.5}$ | Highly active catalyst | 280 | 53.0 | 86.6 | 45.9 |
| | $V_{0.5}$ | Deactivated catalyst | 340 | 39.9 | 80.1 | 32.0 |
| | | Regenerated catalyst | 280 | 54.7 | 86.0 | 47.0 |

We claim:

1. A method for regenerating a phosphorus-, molybdenum- and alkali metal-containing oxidation catalyst spent in the production of an unsaturated carboxylic acid by vapor-phase oxidation of an unsaturated aldehyde, which comprises:
   (a) treating the catalyst with aqueous ammonia containing 6 to 100 moles of ammonia per 12 gram atoms of molybdenum; and thereafter
   (b) treating the catalyst with an aqueous solution containing 0.5 to 60 moles of an amine or ammonium carbonate per 12 gram atoms of molybdenum; and
   (c) drying and calcining the treated catalyst.

2. A method according to claim 1, wherein the aqueous ammonia also contains up to 5 moles of ammonium nitrate per 12 gram atoms of molybdenum.

3. A method according to claim 1, wherein the aqueous ammonia also contains up to 7 moles of hydrogen peroxide or ozone per 12 gram atoms of molybdenum.

4. A method according to claim 1, wherein the aqueous ammonia also contains up to 5 moles of ammonium nitrate and up to 7 moles of hydrogen peroxide or ozone per 12 gram atoms of molybdenum.

5. A method according to claim 1, wherein the catalyst in step (b) is treated with ammonium carbonate.

6. A method according to claim 1, wherein the catalyst in step (b) is treated with an amine.

7. A method according to claim 6, wherein the amine is a heterocyclic compound.

8. A method according to claim 1, wherein the catalyst is dried between steps (a) and (b).

9. A method according to claim 1, wherein after said catalyst is treated with aqueous ammonia of step (a), the aqueous solution of step (b) is added thereinto.

10. A method according to claim 4, wherein the catalyst is dried between steps (a) and (b).

11. A method according to claim 4, wherein after said catalyst is treated with aqeuous ammonia of step (a), the aqueous solution of step (b) is added thereinto.

* * * * *